United States Patent [19]

D'Silva

[11] 4,072,750

[45] Feb. 7, 1978

[54] 1,3,5-TRITHIANE AND 1,3,5-OXADITHIANE CARBAMOYLOXIME COMPOUNDS AND INSECTICIDAL AND MITICIDAL COMPOSITIONS AND METHODS EMPLOYING THEM

[75] Inventor: Themistocles D. J. D'Silva, South Charleston, W. Va.

[73] Assignee: Union Carbide Corporation, New York, N.Y.

[21] Appl. No.: 691,396

[22] Filed: June 1, 1976

[51] Int. Cl.$^2$ ................ C07D 341/00; C07D 327/00; A61K 31/39; A61K 31/385

[52] U.S. Cl. .................................. 424/276; 424/277; 260/327 T

[58] Field of Search ...................... 260/327 M, 327 T; 424/276, 277

[56] References Cited

U.S. PATENT DOCUMENTS

| | | | |
|---|---|---|---|
| 3,066,149 | 11/1962 | Slezak et al. | 260/327 |
| 3,193,561 | 7/1965 | Addor | 260/327 |
| 3,365,361 | 1/1968 | Addor | 167/33 |
| 3,467,672 | 9/1969 | Addor | 260/327 |
| 3,661,930 | 5/1972 | Ghosh et al. | 260/327 R |
| 3,678,075 | 7/1972 | Nikles | 260/327 M |
| 3,770,769 | 11/1973 | Schneider | 260/327 M |
| 3,832,400 | 8/1974 | Meyer et al. | 260/566 AC |
| 3,875,232 | 4/1975 | Magee | 260/566 |
| 3,928,382 | 12/1975 | Addor et al. | 260/327 M |
| 3,956,500 | 5/1976 | Durden et al. | 424/276 |

*Primary Examiner*—Cecilia M. S. Jaisle
*Attorney, Agent, or Firm*—Richard C. Stewart

[57] ABSTRACT

1,3,5-Trithiane and 1,3,5-oxadithiane carbamoyloximes exhibit outstanding pesticidal activity.

44 Claims, No Drawings

1,3,5-TRITHIANE AND 1,3,5-OXADITHIANE CARBAMOYLOXIME COMPOUNDS AND INSECTICIDAL AND MITICIDAL COMPOSITIONS AND METHODS EMPLOYING THEM

This invention relates to a novel class of carbamoyloxime compounds and to their preparation. This invention is also directed to insecticidal and miticidal compositions comprising an acceptable carrier and an insecticidally and miticidally effective amount of a compound of this invention and to a method of controlling insects and mites by subjecting them to an insecticidally or miticidally effective amount of a compound of this invention.

More particularly, this invention relates to compounds of the formula:

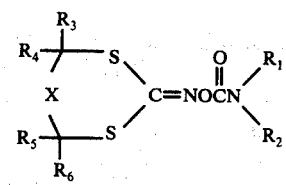

wherein:
$R_1$ and $R_2$ are individually hydrogen, alkyl, cycloalkyl or substituted alkyl or cycloalkyl, wherein the permissible substituents are one or more fluoro, chloro, bromo, nitro, cyano or alkoxy substituents;
$R_3$, $R_4$, $R_5$ and $R_6$ are individually hydrogen or alkyl;
X is oxygen, sulfur, sulfinyl or sulfonyl.

In general, the total number of aliphatic carbon atoms included in any $R_1$, $R_2$, $R_3$, $R_4$, $R_5$ and $R_6$ substituent may not exceed six. Preferred because of their higher level of pesticidal activity are the compounds of this invention in which $R_1$, $R_2$, $R_3$, $R_4$, $R_5$, and $R_6$ are individually hydrogen or alkyl having from 1 to 4 carbon atoms.

The compounds of this invention exhibit outstanding miticidal and insecticidal activities. They are relatively non-toxic to plants and mammals when used in amounts sufficient to kill insects and mites.

The compounds of this invention can be prepared in accordance with a variety of methods. Four preferred methods are illustrated by the reaction schemes set forth below in which $R_1$, $R_2$, $R_3$, $R_4$, $R_5$, $R_6$ and X are as described above and Y is chlorine or fluorine, except as noted.

METHOD I

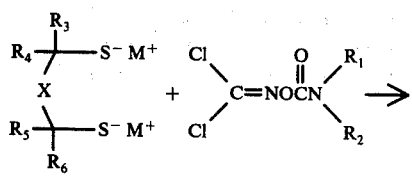

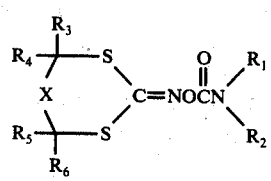

METHOD II

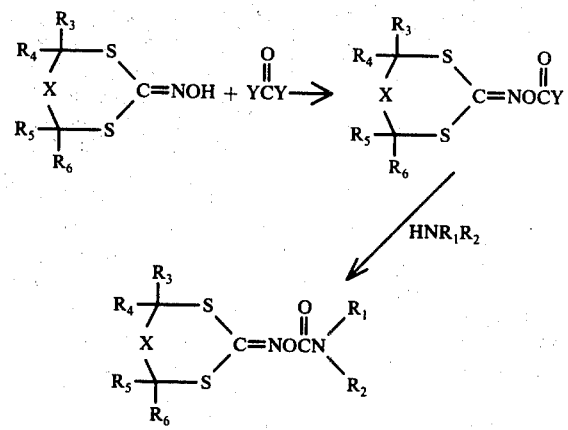

METHOD III

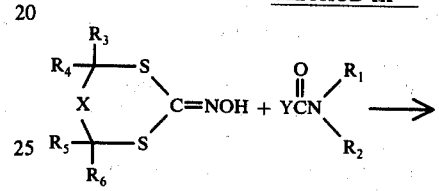

METHOD IV

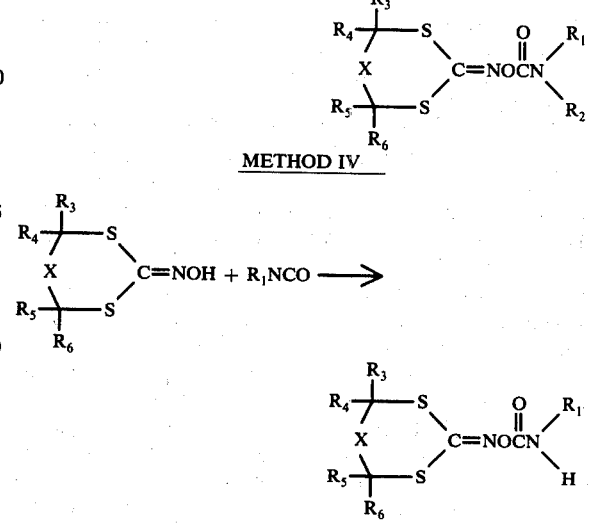

$R_1$ in Method IV is substituted or unsubstituted alkyl or cycloalkyl.

The reactions illustrated in Methods I, II, III and IV are conducted under similar reaction conditions. Substantially equimolar amounts of the reactants are brought together in an inert solvent. Any inert solvent such as benzene, toluene, xylene, dioxane, tetrahydrofuran or the like can be used.

Reaction temperatures and pressures are not critical. Reaction tempertures of from about $-30°$ C to about $100°$ C produce satisfactory results. For convenience the reaction is usually conducted at atmosphereic or autogenous pressure.

These reactions can be conducted in either a homogenous phase system or a heterogenous phase system. In the latter case phase transfer agents, such as crown ethers, quaternary ammonium halide compounds or the like may be used to facilitate the transfer of the reactants across the interface.

The reactions illustrated in Methods II and III are conducted in the presence of an acid acceptor. The acid acceptor employed can be either an organic or an inorganic base. Illustrative of organic bases which are useful as acid acceptors are tertiary amines, alkali metal alkoxides or the like. Inorganic bases such as potassium hydroxide, sodium hydroxide or the like can be used as acid acceptors. Preferred acid acceptors are tertiary amines such as pyridine, triethylamine, 1,4-diazabicyclo [2.2.2] octane or the like. The molar ratio of acid acceptor to either reactant is substantially equimolar or a slight excess of acid acceptor may be employed.

The reaction illustrated in Method IV is preferably conducted in the presence of a catalyst. In general, any conventional catalyst of the type commonly employed to promote reactions between isocyanate compounds and compounds which contain an active hydrogen can be used. Preferred catalysts are tertiary amines such as triethylamine or the like. The reaction is conducted in the presence of a quantity of catalyst sufficient to provide a suitable and reasonable reaction rate.

Compounds according to this invention wherein X is sulfinyl or sulfonyl can be prepared by the selective oxidation of the 5-sulfide linkage of the corresponding 1,3,5-trithiane carbamate or oxime precursor with a mild oxidising agent, such as peracetic acid.

O-carbamoyl dichloroformaldoxime precursors can be prepared by reacting the corresponding phosgene oxime with an appropriately substituted carbamic acid halide as disclosed in U.S. Pat. No. 3,553,264. Oxadithia mercaptide salts can be prepared by treating the corresponding bis-(dithioacetate alkyl) ether with an alkali metal hydroxide and trithia mercaptide salts can be prepared by treating the corresponding 1,3-dimercapto alkyl sulfide with either an alkali metal hydroxide or an alkali metal alkoxide. Substituted bis-(acetylthioalkyl)ethers are known compounds and substituted 1,3-dimercaptoalkyl sulfides can be obtained by reacting appropriately substituted aldehydes and/or ketones with hydrogen sulfide. The latter procedure is disclosed in J. Am. Chem. Soc., 74, 3982 (1952).

Isocyanate, carbonyl halide and amine precursors are well known compounds.

The carbamoyl halide precursors used in the preparation of the compounds of this invention can be prepared by reacting an appropriately substituted amine with a carbonyl halide such as phosgene in the presence of an acid acceptor such as triethylamine.

Oxime precursors can be prepared by sequentially reacting the corresponding 1,3,5-oxadithiane or 1,3,5-trithiane compound with an acid acceptor and a nitrite ester followed by the addition of a neutralizing acid. For example, 2-oximino-1,3,5-trithiane can be prepared by sequentially reacting 1,3,5-trithiane with butyl lithium and ethyl nitrite followed by neutralization with concentrated hydrochloric acid.

1,3,5-Trithiane and 1,3,5-oxadithiane compounds used in the preparation of oxime precursors can be prepared according to conventional methods. For example, oxadithiane heterocyclic precursors can be prepared by condensing the corresponding bis(mercaptoalkyl)ether with dihalomethane. Trithiane heterocyclic precursors can be prepared by condensing either the corresponding bis-(mercaptoalkyl)sulfide with dihalomethane or by condensing an appropriately substituted aldehyde with hydrogen sulfide. The above described procedures are disclosed in more detail in U.S. Pat. No. 2,595,173, German Pat. No. 762,037, T. A. Stanfield and L. B. Reynolds, Jr., J. Amer. Chem. Soc., 74, 2878 (1952), E. Campaign et al. J. Org. Chem. 27, 135 (1962) and references cited therein.

The following specific examples are presented to more particularly illustrate the invention.

EXAMPLE I

Preparation of 2-Oximino-1,3,5-trithiane

To a slurry of 27.6 grams of 1,3,5-trithiane in 500 ml of anhydroous tetrahydrofuran stirring at $-25°$ C under nitrogen, was added 130 ml of a 1.6 M solvent of butyl lithium in hexane over a period of forty minutes. The cold mixture was stirred for four hours at $-15°$ C. The mixture was then added over a 75 minute period to a solution of 24 grams of ethyl nitrite dissolved in 150 ml of tetrahydrofuran held at $-25°$ C. The reaction mixture was then allowed to warm to ambient temperature and then stirred for 18 hours. The reaction mixture was then cooled to $10°$ C and neutralized with a solvent of 20 ml of concentrated hydrochloric acid dissolved in 80 ml of ethanol. The resulting slurry was concentrated at reduced presure to 300 ml and poured into a mixture of 300 ml of water and 500 ml of ether. The phases were allowed to equilibrate and then filtered. The filtrate was separated into water and ether phases. The water phase was extracted with 500 ml of ether. The two ether portions were combined and dried over $M_gSO_4$. The ether phase was evaporated under reduced pressure to yield 16 g of a thick oil which solidified on standing. Recrystallization from 200 ml of hot toluene yielded 9.2 grams of 2-oximino-1,3,5-trithiane, mp $105°-107°$ C.

Analysis:

Calc'd. for $C_3H_5NOS_3$: C,21.54; H:3.01; N:8.37

Found: C, 21.85; H: 2.98; N: 8.38

NMR (acetone-$d_6$): $\delta$ 4.27 (S) ($CH_2$); $\delta$ 4.30 (S), $CH_2$ and $\delta$ 11.73 (S), NOH.

IR (KBr): 3.2, 3.4, 6.3, 7.0–7.4 8.6, 9.1 and 10.5 $\mu$.

EXAMPLE II (Method I)

Preparation of 2-Methylcarbamoyl oximino-1,3,5-trithiane

To a solution of sodium (1.89g) in methanol (50ml) was added slowly at $10°-15°$ C bis-mercaptomethyl sulfide (5.16g). After stirring for 15 minutes, the mixture was cooled to $0°$ C and 0-(methylcarbamoyl)dichloroformaldoxime (7.0g) was added dropwise with stirring over a period of 1 hour. After stirring for an additional hour, the product was isolated by extracting methyl acetate. Weight of crude product was 2.7g. The crude reaction product was purified by chromatographic methods and finally crystallized from acetone m.p. $125°-127°$ C.

Analysis:

Calc'd for $C_5H_8N_2O_2S_3$: C,26.77; H, 3.59; N, 12.49

Found: C, 26,89; H, 3.76; N, 12.35

IR (KBr): 3.0 (NH), 5.78 (CO), 6.6, 8.05, 9.0, 9.92 and 10.78$\mu$.

NMR ($CDCl_3$): $\delta$2.91 (d), J~4.8 $H_z$, $CH_3$; $\delta$4.17 (S), $CH_2$; $\delta$4.19 (S), $CH_2$ and broad peak at $\delta$6.05 (1H), NH.

See also Example VI.

EXAMPLE III

Preparation of 4-Methylcarbamoyl oximino-1,3,5-oxadithiane

To a solution of sodium hydroxide (3.8g) in ethanol (125ml) cooled to 5° C, under nitrogen, was added bis-thioacetate methyl ether (9.2g). After stirring for 10 minutes at 0°, the reaction mixture was diluted with 50ml of toluene and 8.0g of O-(methylcarbamoyl) dichloroformaldoxime dissolved in 50ml of toluene was added dropwise with cooling and stirring. The reaction mixture was stirred at 0°-3° C for 4 hours and kept at ambient temperature for 18 hours. The solvents were removed under reduced pressure, diluted with water and ethyl actate and acidified with hydrochloric acid. The ethyl acetate extract was dried and concentrated. Weight of the crude residue was 8.5g. The crude residue was purified by column chromatography and crystalized from ethyl acetate-isopropyl ether to yield a solid with a m.p. of 99°-102° C.

Analysis:

Calc'd for $C_5H_8N_2S_2O_3$; C, 28.83; H, 3.87; N, 13.46
Found: C, 28.80; H, 3.80; N, 13.50
IR(KBr): 2.94 (NH), 5.75 (CO), 6.62, 7.5, 8.1, 8.93, 9.31, 10.62, 11.16, 13.18 and 13.68 $\mu$
NMR ($CDCl_3$): $\delta2,89$ (d), J~4.8 $H_z$, $CH_3$; $\delta5.23$ (S) (4H), $CH_2$ and $\delta6.1$ (broad) (1H), NH.

EXAMPLE IV

Preparation of 2-(methylcarbamoyl oximino)-1, 3, 5-trithiane - 5- oxide

To a solution of 1.0g of 2-methylcarbamoyloximino-1,3,5-trithiane in 50ml of ethyl acetate was added 1.33g of a 22.3 percent solution of peracetic acid. A precipitate formed and was filtered to yield 0.87g of the sulfoxide, m.p. 175°-177° C.

Analysis:

Calc'd. for $C_5H_8N_2O_3S_3$: C, 24.99, H, 3.35; N, 11.65
Found: C, 24.80, H, 3.31; N, 11.20

EXAMPLE V

Preparation of 2-(methylcarbamoyl oximino)-1, 3, 5-trithiane - 5,5-dioxide 2-(Methylcarbamoyloximino)-1,3,5-trithiane-5-oxide prepared by the method of Example IV was further reacted with 5 ml of peracetic acid and left standing for 18 hours at room temperature. Concentrating under reduced pressure yielding 0.15g of a solid residue. Crystallization from acetonitrile yielded a solid, m.p. 174°-177° C (decomp.)

Analysis:

Calc'd for $C_5H_8N_2O_4S_3$: C, 23.43; H, 3.15; N, 10.92
Found: C, 23.70; H, 3.10; N, 10.80

EXAMPLE VI (Method III)

Preparation of 2-(methylcarbamoyloximino)-1,3,5-trithiane

A quantity of 3.3 g of 2-oximino-1,3,5-trithiane and 1.29 ml of methyl isocyanate were dissolved in 50 ml of acetone containing 0.05 ml of triethylamine in a glass pressure vessel. The reaction mixture was allowed to stand for 72 hours at ambient temperature. The solvent was then evaporated and the residue taken up in 200 ml of ethyl acetate. The solution was washed with water, dried over magnesium sulfate and the solvent evaporated off. Recrystallization from isopropyl ether/acetone yielded 2.47 g of 2-methylcarbamoyloximino-1,3,5-trithiane, mp 129°-130°. The compound is identical in spectral properties to that obtained in Example II.

The following compounds are representative of other compounds that are within the scope of this invention which can be prepared according to this invention by selecting appropriate starting materials for use in the procedures described above:

2-(N-Cyanoethyl-N-methylcarbamoyloximino)-1,3,5-trithiane.
4(N-Butyl-N-methylcarbamoyloximino)-1,3,5-oxadithiane.
4-(N,N-dimethylcarbomoyloximino)-1,3,5-trithiane-1,1-dioxide.
2-(N,N-Dimethylcarbamoyloximino)-4,6-dimethyl-1,3,5-trithiane.
4-(N,N-Dimethylcarbamoyloximino)-1,3,5-oxadithiane.
4-(N-Isopropyl-N-methylcarbamoyloximino)-1,3,5-trithiane-1,1-dioxide.
4-(N-Isopropyl-N-methylcarbamoyloximino)-1,3,5-trithiane-1-oxide
2-(N-Nitroethyl-N-methylcarbamoyloximino)-1,3,5-trithiane.
2-(N-Propyl-N-methylcarbamoyloximino)-4,6-dimethyl-1,3,5-trithiane.
4-[N-(2'-Chloroethyl)-N-methylcarbamoyloximino]-2,6-dipropyl-1,3,5-oxadithiane.
4-[N-(2'-Methoxyethyl)-N-methylcarbamoyloximino]-1,3,5-trithiane-1-oxide.
4-(Methylcarbamoyloximino)-1,3,5-oxadithiane.
2-(Methylcarbamoyloximino)-1,3,5-trithiane.
2-[N-Methylcarbamoyloximino]-4,6-dimethyl-1,3,5-trithiane.
2[-N-Methylcarbamoyloximino]-4,4,6,6-tetrehexyl-1,3,5-trithiane.
4-(N-Hexyl-N-Methylcarbamoyloximino)-1,3,5-oxadithiane.
4-(N-Cyclohexyl-N-n-butylcarbamoyloximino)-1,3,5-oxadithiane.
2-(Carbamoyloximino)-1,3,5-trithiane.

Selected species of the new compounds were evaluated to determine their pesticidal activity against mites and certain insects, including an aphid, a boll weevil, a caterpillar, a beetle and a fly.

Suspensions of the test compounds were prepared by dissolving one gram of compound in 50 milliliters of acetone in which had been dissoled 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight employed in the tests described hereinbelow were obtained by appropriate dilutions of the stock suspension with water. The test procedures were as follows.

BEAN APHID FOLIAGE SPRAY TEST

Adults and nymphal stages of the bean aphid (*Aphis fabae* Scop.) reared on potted dwarf nasturtium plants at 65°-70° F and 50-70 per cent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 per cent, respectively. Aphids which fell onto the paper and were unable to remain standing after being uprighted were considered dead. Aphids remaining on the plants were observed closely for movement and those which were unable to move the length of the body upon stimulator by prodding were considered dead. Per cent mortality was recorded for various concentration levels.

Southern Armyworm Leaf Spray Test

Larvae of the southern armyworm (*Prodenia Eridania*, (Cram.), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig. air pressure.

This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead. Per cent mortality was recorded for various concentration levels.

Mexican Bean Beetle Leaf Spray Test

Fourth instar larvae of the Mexican bean beetle (*Epilachna Varivestis, Muls.*), reared on Tendergreen bean plants at a temperature of 80°±5° F. and 50±5 per cent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5°F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.) reared according to the specifications of the Chemical Specialties Manufacturing Association (Blue Book, McNair-Dorland Co., NY., 1954; pages 243-244, 261) under controlled conditions of 80°±5° F. and 50±5 per cent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 per cent (by weight) sugar solution to give a suspension containing 500 parts of test compound per million parts of final formulation, by weight. Ten milliliters of the test formulation were added to a souffle cup containing a one inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 per cent. Flies which showed no sign of movement on prodding were considered dead.

Mite Foliage Spray Test

Adults and nymphal stages of the two-spotted mite (*Tetranychus urticae Koch*), reared on Tendergreen bean plants at 80°±5 per cent relative humidity, were the test organisms. Infested leaves from a stock culture were placed on the primary leaves of two bean plants six to eight inches in height, growing in a two- and-a-half inch clay pot. 150-200 mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted for 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding, was considered living.

The results of these tests are set forth in Table I below. In these tests the pesticidal activity of the compounds against aphid, mite, Sourthern Armyworm, Mexican Bean Beetle, and house fly was ratd as follows:
- A = Excellent control
- B = Partial control
- C = No control The results of all of these tests are set forth in Table I below:

TABLE I
BIOLOGICAL DATA

| STRUCTURE | APHID | MITE | SOUTHERN ARMY-WORM | MEXICAN BEAN-BEETLE | HOUSE FLY |
|---|---|---|---|---|---|
| (S-S-S ring, C=NOCN(CH₃)H, O) | A | A | A | A | A |
| (S-S-O ring, C=NOCN(CH₃)H, O) | A | A | A | A | A |
| (S-S ring, O=S, C=NOCN(CH₃)H, O) | A | A | A | A | A |
| (S-S ring, O=S=O, C=NOCN(CH₃)H, O) | — | — | C | B | A |

The compounds contemplated in this invention may be applied as insecticides, mitricides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surfaces active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generlly, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 per cent by weight and in the solid formulations from about 0.5 to about 90 per cent by weight. Satisfactory sprays, dusts, or granules for general use contain from about one-fourth to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule. and they may be used in the soil, upon the seeds, or the roots of plants without injuring either the seeds or roots of plants. They may also be used in combination with other pesticidally active compounds.

What is claimed is:
1. A compound of the formula:

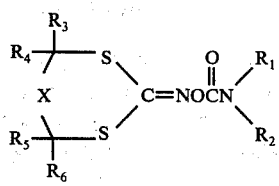

wherein:

$R_1$ and $R_2$ are individually hydrogen, alkyl, cycloalkyl or substituted alkyl or cycloalkyl wherein the permissible substituents are one or more fluoro, chloro, bromo, cyano, nitro or alkoxy substituents; $R_3$, $R_4$, $R_5$ and $R_6$ are individually hydrogen or alkyl; X is oxygen, sulfur, sulfinyl or sulfonyl; with the proviso that $R_1$, $R_2$, $R_3$, $R_4$, $R_5$ and $R_6$ substituents may not individually include more than 6 carbons.

2. A compound according to claim 1 wherein $R_1$ and $R_2$ are individually hydrogen or alkyl.

3. A compound according to claim 1 wherein $R_1$ and $R_2$ are individually hydrogen or alkyl having from 1 to 4 carbons.

4. A compound according to claim 1 wherein $R_1$ is alkyl having from 1 to 4 carbons and $R_2$ is hydrogen.

5. A compound according to claim 1 wherein $R_1$ is methyl and $R_2$ is hydrogen.

6. A compound according to claim 1 wherein X is oxygen.

7. A compound according to claim 1 wherein X is sulfur.

8. A compound according to claim 1 wherein X is sulfinyl.

9. A compound according to claim 1 wherein X is sulfonyl.

10. A compound according to claim 1 wherein $R_3$, $R_4$, $R_5$ and $R_6$ are individually hydrogen or alkyl having from 1 to 4 carbons.

11. A compound according to claim 1 wherein $R_3$, $R_4$, $R_5$ and $R_6$ are individually hydrogen or methyl.

12. A compound according to claim 1 wherein $R_3$, $R_4$, $R_5$ and $R_6$ are hydrogen.

13. A compound according to claim 1 wherein $R_1$, $R_2$, $R_3$, $R_4$, $R_5$ and $R_6$ are individually hydrogen or alkyl having from 1 to 4 carbons.

14. 2-Methylcarbamoyloximino-1,3,5-trithiane.

15. 4-Methylcarbamoyloximino-1,3,5-oxadithiane.

16. An insecticidal and miticidal composition comprising an acceptable carrier and an insecticidally or miticidally effective amount of a compound of the formula:

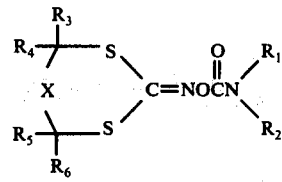

wherein:
$R_1$ and $R_2$ are individually hydrogen, alkyl, cycloalkyl or substituted alkyl or cycloalkyl wherein the permissible substitutents are one or more chloro, fluoro, bromo, nitro, cyano or alkoxy substitutents; $R_3$, $R_4$, $R_5$ and $R_6$ are individually hydrogen or alkyl; X is oxygen, sulfur, sulfinyl or sulfonyl; with the proviso that $R_1$, $R_2$, $R_3$, $R_4$, $R_5$ and $R_6$ substituents may not individually include more than six carbons.

17. A composition according to claim 16 wherein $R_1$ and $R_2$ are individually hydrogen or alkyl.

18. A composition according to claim 16 wherein $R_1$ and $R_2$ are individually hydrogen or alkyl having from 1 to 4 carbons.

19. A composition according to claim 16 wherein $R_1$ is alkyl having from 1 to 4 carbons and $R_2$ is hydrogen.

20. A composition according to claim 16 wherein $R_1$ is methyl and $R_2$ is hydrogen.

21. A composition according to claim 16 wherein X is oxygen.

22. A composition according to claim 16 wherein X is sulfur.

23. A composition according to claim 16 wherein X is sulfinyl.

24. A composition according to claim 16 wherein X is sulfonyl.

25. A composition according to claim 16 wherein $R_3$, $R_4$, $R_5$ and $R_6$ are individually hydrogen or alkyl having from 1 to 4 carbons.

26. A composition according to claim 16 wherein $R_3$, $R_4$, $R_5$ and $R_6$ are individually hydrogen or methyl.

27. A composition according to claim 16 wherein $R_3$, $R_4$, $R_5$ and $R_6$ are hydrogen.

28. A composition according to claim 16 wherein the active toxicant is 2-methylcarbamoyloximino-1,3,5-trithiane.

29. A composition according to claim 16 wherein the active toxicant is 4-methylcarbamoyloximono-1,3,5-oxadithiane.

30. A method of controlling insects and mites which comprises subjecting them to an insecticidally or miticidally effective amount of a compound of the formula:

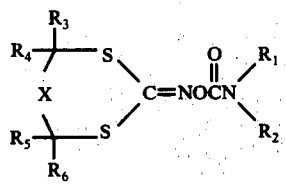

wherein:
$R_1$ and $R_2$ are individually hydrogen, alkyl, cycloalkyl or substituted alkyl or cycloalkyl wherein the permissible substituents are one or more chloro, bromo, fluoro, cyano, nitro or alkoxy substituents; $R_3$, $R_4$, $R_5$ and $R_6$ are individually hydrogen or alkyl; X is oxygen, sulfur, sulfinyl or sulfonyl; with the proviso that $R_1$, $R_2$, $R_3$, $R_4$, $R_5$ and $R_6$ substituents may not individually include more than six carbons.

31. A method according to claim 30 wherein $R_1$ and $R_2$ are individually hydrogen or alkyl.

32. A method according to claim 30 wherein $R_1$ and $R_2$ are individually hydrogen or alkyl having from 1 to 4 carbons.

33. A method according to claim 30 wherein $R_1$ is alkyl having from 1 to 4 carbons and $R_2$ is hydrogen.

34. A method according to claim 30 wherein $R_1$ is methyl and $R_2$ is hydrogen.

35. A method according to claim 30 wherein X is oxygen.

36. A method according to claim 30 wherein X is sulfur.

37. A method according to claim 30 wherein X is sulfinyl.

38. A method according to claim 30 wherein X is sulfonyl.

39. A method according to claim 30 wherein $R_3$, $R_4$, $R_5$ and $R_6$ are individually hydrogen or alkyl having from 1 to 4 carbons.

40. A method according to claim 30 wherein $R_3$, $R_4$, $R_5$ and $R_6$ are individually hydrogen or methyl.

41. A method according to claim 30 wherein $R_3$, $R_4$, $R_5$ and $R_6$ are hydrogen.

42. A method according to claim 30 wherein $R_1$, $R_2$, $R_3$, $R_4$, $R_5$ and $R_6$ are individually hydrogen or alkyl having from 1 to 4 carbons.

43. A method according to claim 30 wherein the compound is 2-methylcarbamoyloximino-1,3,5-trithiane.

44. A method according to claim 30 wherein the compound is 4-methylcarbamoyloximino-1,3,5-oxadithiane.

* * * * *

UNITED STATES PATENT OFFICE
CERTIFICATE OF CORRECTION

Patent No. 4,072,750             Dated February 7, 1978

Inventor(s) Themistocles D.J. D'Silva

It is certified that error appears in the above-identified patent and that said Letters Patent are hereby corrected as shown below:

Column 5, line 51 which reads --yielding-- should read "yielded".

Column 6, line 50, which reads --dissoled-- should read, "dissolved".

Column 9, line 7, which reads --Sourthern-- should read "Southern".

Column 9, line 8, which reads --ratd-- should read "rated".

Signed and Sealed this

Third Day of October 1978

[SEAL]

Attest:

RUTH C. MASON  
Attesting Officer

DONALD W. BANNER  
Commissioner of Patents and Trademarks